US012636460B2

(12) United States Patent
Pan et al.

(10) Patent No.: US 12,636,460 B2
(45) Date of Patent: May 26, 2026

(54) TEMPERATURE CONTROL METHOD AND SYSTEM FOR HEATED BREATHING-CIRCUIT, AND BREATHING ASSISTANCE APPARATUS THEREOF

(71) Applicant: RESVENT MEDICAL TECHNOLOGY CO., LTD, Shenzhen (CN)

(72) Inventors: Haiyang Pan, Shenzhen (CN); Rongrong Zhu, Shenzhen (CN)

(73) Assignee: RESVENT MEDICAL TECHNOLOGY CO., LTD, Shenzhen (CN)

( * ) Notice: Subject to any disclaimer, the term of this patent is extended or adjusted under 35 U.S.C. 154(b) by 427 days.

(21) Appl. No.: 18/477,608

(22) Filed: Sep. 29, 2023

(65) Prior Publication Data

US 2024/0216638 A1     Jul. 4, 2024

(30) Foreign Application Priority Data

Dec. 29, 2022    (CN) .......................... 202211712357.3

(51) Int. Cl.
A61M 16/00          (2006.01)
A61M 16/10          (2006.01)
(Continued)

(52) U.S. Cl.
CPC .... A61M 16/1075 (2013.01); A61M 16/0003 (2014.02); A61M 16/024 (2017.08); A61M 2205/3368 (2013.01)

(58) Field of Classification Search
CPC ............ A61M 16/1075; A61M 16/003; A61M 16/024; A61M 2205/3368
See application file for complete search history.

(56) References Cited

U.S. PATENT DOCUMENTS 4,248,217 A * 2/1981 Brisson ............. A61M 16/1075
                                                 128/203.27
2009/0306529 A1* 12/2009 Curti ................... A61B 5/4818
                                                 128/204.23
2014/0116433 A1* 5/2014 Ghalib .................. A61M 16/16
                                                 128/203.14

FOREIGN PATENT DOCUMENTS

WO      WO-2017043981 A1 * 3/2017     ........ A61M 16/0891
WO      WO-2017126980 A2 * 7/2017     ............ A61M 16/16
WO      WO-2022203523 A1 * 9/2022     ............ A61M 16/16

* cited by examiner

*Primary Examiner* — Randy W Gibson
(74) *Attorney, Agent, or Firm* — Hemisphere Law, PLLC

(57)          ABSTRACT

A temperature control method for a heated breathing-circuit includes steps of: continuously controlling the heated breathing-circuit to be heated continuously in a first predetermined time period; obtaining a sampling temperature signal of the heated breathing-circuit in a second predetermined time period; obtaining a resistance value of a temperature sensing loop by converting the sampling temperature signal; controlling the temperature-sampling circuit to be electrically connected with the short-circuit loop in a third predetermined time period, to obtain an internal resistance value of the temperature-sampling circuit; obtaining a resistance value of the temperature sensor thought the resistance value of the temperature sensing loop, a resistance value of the resistance wire, and the internal resistance; and calculating the resistance value of the temperature sensor and the temperature of the temperature sensor, to obtain an actual temperature value of the heated breathing-circuit. A temperature control system for a heated breathing-circuit is also provided.

20 Claims, 5 Drawing Sheets

(51) Int. Cl.
    *A61M 16/12*         (2006.01)
    *A61M 16/16*         (2006.01)

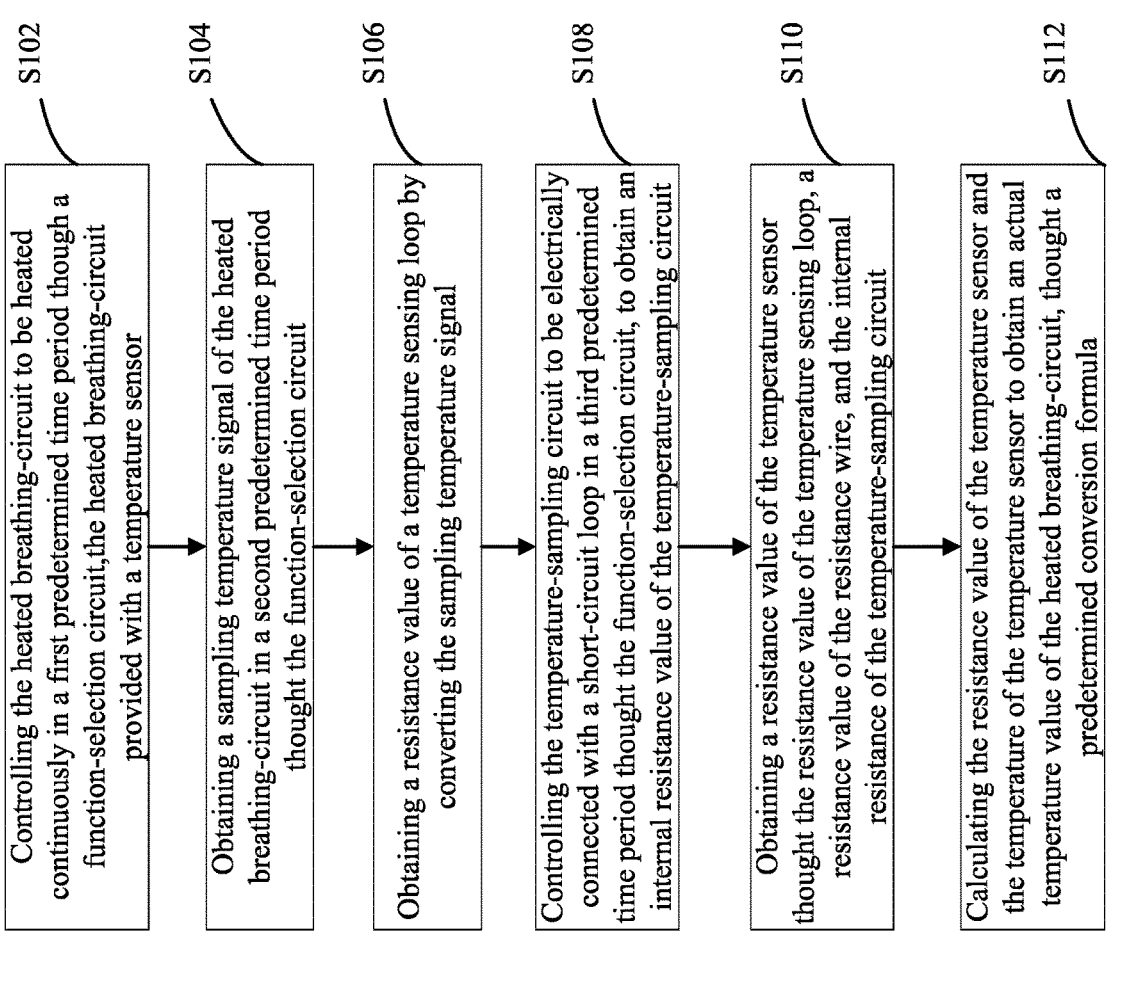

S102

Controlling the heated breathing-circuit to be heated continuously in a first predetermined time period though a function-selection circuit,the heated breathing-circuit provided with a temperature sensor

S104

Obtaining a sampling temperature signal of the heated breathing-circuit in a second predetermined time period thought the function-selection circuit

S106

Obtaining a resistance value of a temperature sensing loop by converting the sampling temperature signal

S108

Controlling the temperature-sampling circuit to be electrically connected with a short-circuit loop in a third predetermined time period thought the function-selection circuit, to obtain an internal resistance value of the temperature-sampling circuit

S110

Obtaining a resistance value of the temperature sensor thought the resistance value of the temperature sensing loop, a resistance value of the resistance wire, and the internal resistance of the temperature-sampling circuit

S112

Calculating the resistance value of the temperature sensor and the temperature of the temperature sensor to obtain an actual temperature value of the heated breathing-circuit, thought a predetermined conversion formula

FIG. 1

TEMPERATURE CONTROL METHOD AND SYSTEM FOR HEATED BREATHING-CIRCUIT, AND BREATHING ASSISTANCE APPARATUS THEREOF

CROSS REFERENCE TO RELATED APPLICATION

This non-provisional patent application claims priority under 35 U. S. C. § 119 from Chinese Patent Application No. 2022117123573 filed on Dec. 29, 2022, the entire content of which is incorporated herein by reference.

TECHNICAL FIELD

The disclosure relates to medical equipment technologies, in particular to a temperature control method for a heated breathing-circuit, and a breathing assistance apparatus using the temperature control method.

BACKGROUND

Breathing assistance apparatus (such as ventilators, oxygentherapy apparatus, and the like), include a breathing circuit. The breathing assistance apparatus provided with gaps to users, and the gas is typically humidified before flow to the users via the breathing circuit. In order to prevent humidified gas from forming condensed water in an inner of a breathing circuit, and also to improve comforts of users, a heating device needs to be heat the gas delivered from the breathing circuit to users. Therefore, a gas-temperature sampling device, like a negative temperature coefficient (NTC) thermistor, needs to be provided on a heated breathing-circuit to monitor gas temperature at an outlet end of the heated breathing-circuit accurately, so as to precisely control the gas temperature of the interior of the heated breathing circuit.

In existing temperature control systems for the heated breathing-circuit, resistance values of the NTC thermistors are usually obtained by sampling systems directly. In conditions of different environment temperatures, or different temperatures of printed circuit boards (PCB) of the temperature control systems, there are deviations of temperature-drift and inherent errors of electronic components, in the sampling system. However, the existing systems do not deal with the deviations and it results that there is an error in the obtained resistance values of the NTC thermistors, and a temperature control effect the will be affected.

SUMMARY

In a first aspect, the method of temperature control for the heated breathing-circuit with the temperature correction function is provided. The method includes steps of: controlling the heated breathing-circuit to be heated continuously in a first predetermined time period though a function-selection circuit, the heated breathing-circuit provided with a temperature sensor; obtaining a sampling temperature signal of the heated breathing-circuit in a second predetermined time period thought the function-selection circuit, wherein the heated breathing-circuit is electrically connected with a temperature-sampling circuit thought the function-selection circuit during the second predetermined time period; obtaining a resistance value of a temperature sensing loop by converting the sampling temperature signal; controlling the temperature-sampling circuit to be electrically connected with a short-circuit loop in a third predetermined time period thought the function-selection circuit, to obtain an internal resistance value of the temperature-sampling circuit, the first predetermined time period, the second predetermined time period, and the third predetermined time period form a processing cycle time period; obtaining a resistance value of the temperature sensor thought the resistance value of the temperature sensing loop, a resistance value of the resistance wire, and the internal resistance of the temperature-sampling circuit; and calculating the resistance value of the temperature sensor and the temperature of the temperature sensor to obtain an actual temperature value of the heated breathing-circuit, thought a predetermined conversion formula.

In a second aspect, a breathing assistance apparatus is provided. The breathing assistance apparatus includes a heated breathing-circuit, a temperature-sampling circuit, a short-circuit loop, a microprocessor, and a function-selection circuit. The heated breathing-circuit is provided with a temperature sensor. The temperature-sampling circuit is configured to sample a sampling temperature. The short-circuit loop is configured to make only the temperature-sampling circuit be electrically energized. The function-selection circuit is configured to selectively establish different relationships among the heated breathing-circuit, the temperature-sampling circuit, the short-circuit loop, and the microprocessor; wherein the microprocessor is configured to: controlling the heated breathing-circuit to be heated continuously in a first predetermined time period though the function-selection circuit; obtaining a sampling temperature signal of the heated breathing-circuit in a second predetermined time period thought the function-selection circuit, wherein the heated breathing-circuit is electrically connected with the temperature-sampling circuit thought the function-selection circuit during the second predetermined time period; obtaining a resistance value of a temperature sensing loop by converting the sampling temperature signal; controlling the temperature-sampling circuit to be electrically connected with the short-circuit loop in a third predetermined time period thought the function-selection circuit, to obtain an internal resistance value of the temperature-sampling circuit; the first predetermined time period, the second predetermined time period, and the third predetermined time period form a processing cycle time period; obtaining a resistance value of the temperature sensor thought the resistance value of the temperature sensing loop, a resistance value of the resistance wire, and the internal resistance of the temperature-sampling circuit; and obtaining a resistance value of the temperature sensor thought the resistance value of the temperature sensing loop, a resistance value of the resistance wire, and the internal resistance of the temperature-sampling circuit.

The mention-above method, and breathing assistance apparatus realize measurements of the temperature-sampling circuit by adding the short-circuit loop, which eliminates influences of temperature-drift errors of electronic components of the temperature-sampling circuit on sampling the temperature of the heated breathing-circuit, and improves the accuracy of temperature control.

BRIEF DESCRIPTION OF THE DRAWINGS

In order to illustrate the technical solution in the embodiments of the disclosure or the prior art more clearly, a brief description of drawings required in the embodiments or the prior art is given below. Obviously, the drawings described below are only some of the embodiments of the disclosure.

For ordinary technicians in this field, other drawings can be obtained according to the structures shown in these drawings without any creative effort.

FIG. 1 illustrates a flow diagram of a temperature control method for a heated breathing-circuit.

DETAILED DESCRIPTION OF THE EMBODIMENTS

In order to make the purpose, technical solution and advantages of the disclosure more clearly, the disclosure is further described in detail in combination with the drawings and embodiments. It is understood that the specific embodiments described herein are used only to explain the disclosure and are not configured to define it. On the basis of the embodiments in the disclosure, all other embodiments obtained by ordinary technicians in this field without any creative effort are covered by the protection of the disclosure.

The terms "first", "second", "third", "fourth", if any, in the specification, claims and drawings of this application are configured to distinguish similar objects but need not be configured to describe any particular order or sequence of priorities. It should be understood that the data used here are interchangeable where appropriate, in other words, the embodiments described can be implemented in order other than what is illustrated or described here. In addition, the terms "include" and "have" and any variation of them, can encompass other things. For example, processes, methods, systems, products, or equipment that comprise a series of steps or units need not be limited to those clearly listed, but may include other steps or units that are not clearly listed or are inherent to these processes, methods, systems, products, or equipment.

It is to be noted that the references to "first", "second", etc. in the disclosure are for descriptive purpose only and neither be construed or implied the relative importance nor indicated as implying the number of technical features. Thus, feature defined as "first" or "second" can explicitly or implicitly include one or more such features. In addition, technical solutions between embodiments may be integrated, but only on the basis that they can be implemented by ordinary technicians in this field. When the combination of technical solutions is contradictory or impossible to be realized, such combination of technical solutions shall be deemed to be non-existent and not within the scope of protection required by the disclosure.

Figure 4:
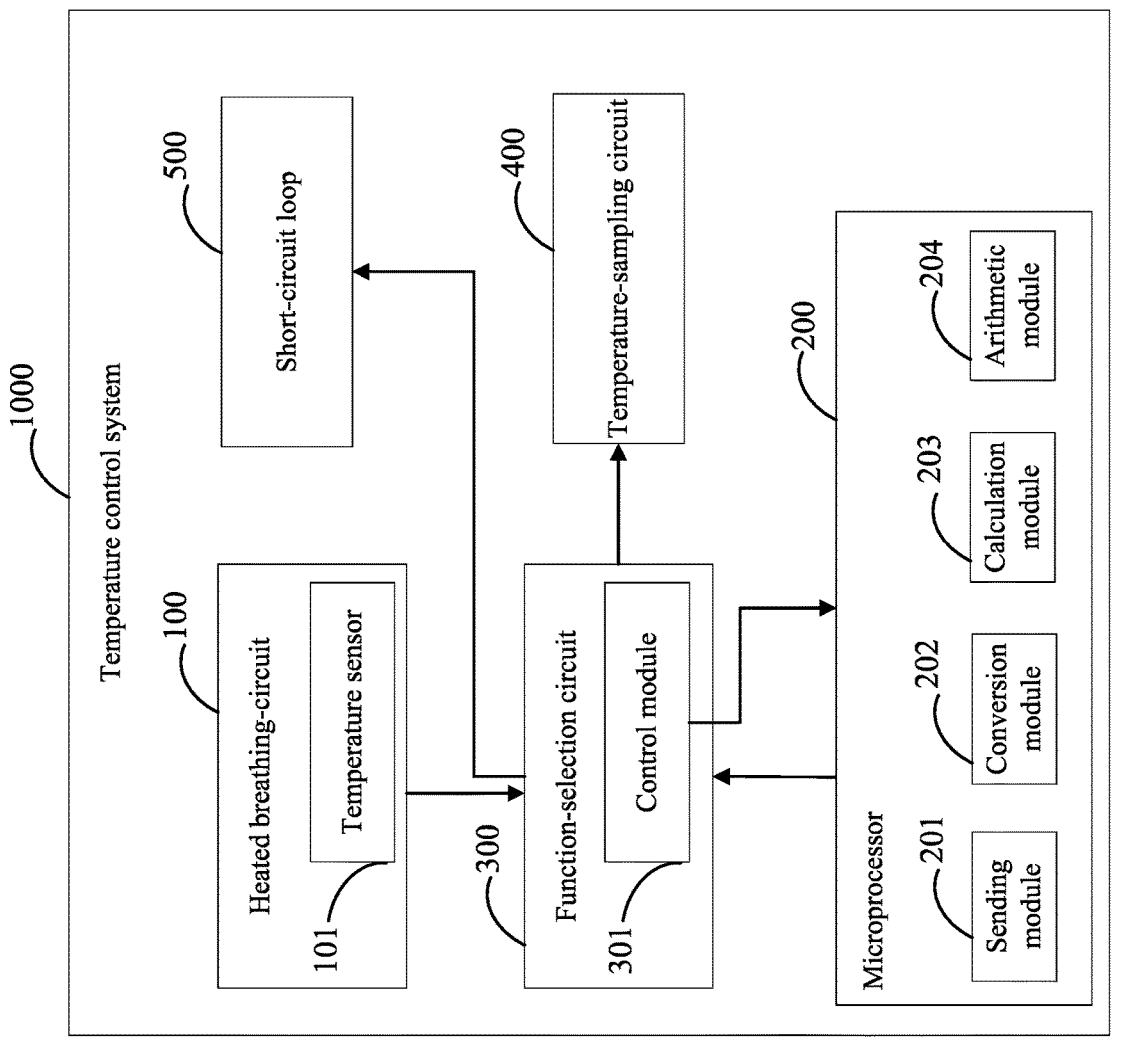
FIG. 4 illustrates a schematic diagram of a temperature control system for a heated breathing-circuit.

Referring to FIG. 1 and FIG. 4, a flow diagram of a temperature control method for a heated breathing-circuit is illustrated in FIG. 1, and a schematic diagram of a temperature control system 1000 for the heated breathing-circuit is illustrated in FIG. 4. The temperature control system 1000 executes program instructions to perform the temperature control method.

The temperature control system 1000 is applied in a breathing assistance apparatus, and includes a heated breathing-circuit 100, a microprocessor 200, a function-selection circuit 300, a temperature-sampling circuit 400, and a short-circuit loop 500. In detail, the heated breathing-circuit 100 includes a temperature sensor 101. The microprocessor 200 includes a sending module 201, a conversion module 202, a calculation module 203, and an arithmetic module 204. The sending module 201 is configured to send instructions to ensure that the heated breathing-circuit 100 is heated in a first predetermined time period. The first predetermined time period is a time of continuously heating the heated breathing-circuit 100. The conversion module 202 is configured to obtain a resistance value of a temperature sensing loop thought a conversion of a temperature signal. The temperature sensing loop is composed of the temperature-sampling circuit 400, the heated breathing-circuit 100, and the temperature sensor 101. The calculation module 203 is configured to obtain a resistance value of the temperature sensor 101 based on the resistance value of the temperature sensing loop, a resistance wire, and an internal resistance of the temperature-sampling circuit 400. The resistance value of the resistance wire is preset in the microprocessor 200. The arithmetic module 204 is configured to calculate the resistance value and a temperature of the temperature sensor 101 using a predetermined conversion formula to obtain an actual temperature of the temperature sensor 10. The function-selection circuit 300 includes a control module 301. The control module 301 is configured to control tasks executed by the microprocessor 200 utilizing time-division multiplexing. The temperature-sampling circuit 400 is electrically connected to the heated breathing-circuit 100 via the function-selection circuit 300. The temperature-sampling circuit 400 is configured to send the temperature signal in the heated breathing-circuit 100 to the microprocessor 200 in second predetermined time period. The second predetermined time period is time of sampling the temperature. The short-circuit loop 500 is electrically connected to the temperature-sampling circuit 400 thought the function-selection circuit 300. The short-circuit loop 500 is configured to obtain an internal resistance value of the temperature-sampling circuit 400 in response to the instructions of the microprocessor 200 in third predetermined time period. The third predetermined time period is time of sampling the internal resistance value. Total time of the first predetermined time period, the second predetermined time period, and the third predetermined time period is time of a processing cycle. The first predetermined time period is the longest time of three types of preset time. The temperature control method for the heated breathing-circuit includes steps S102-S112.

Figure 5:
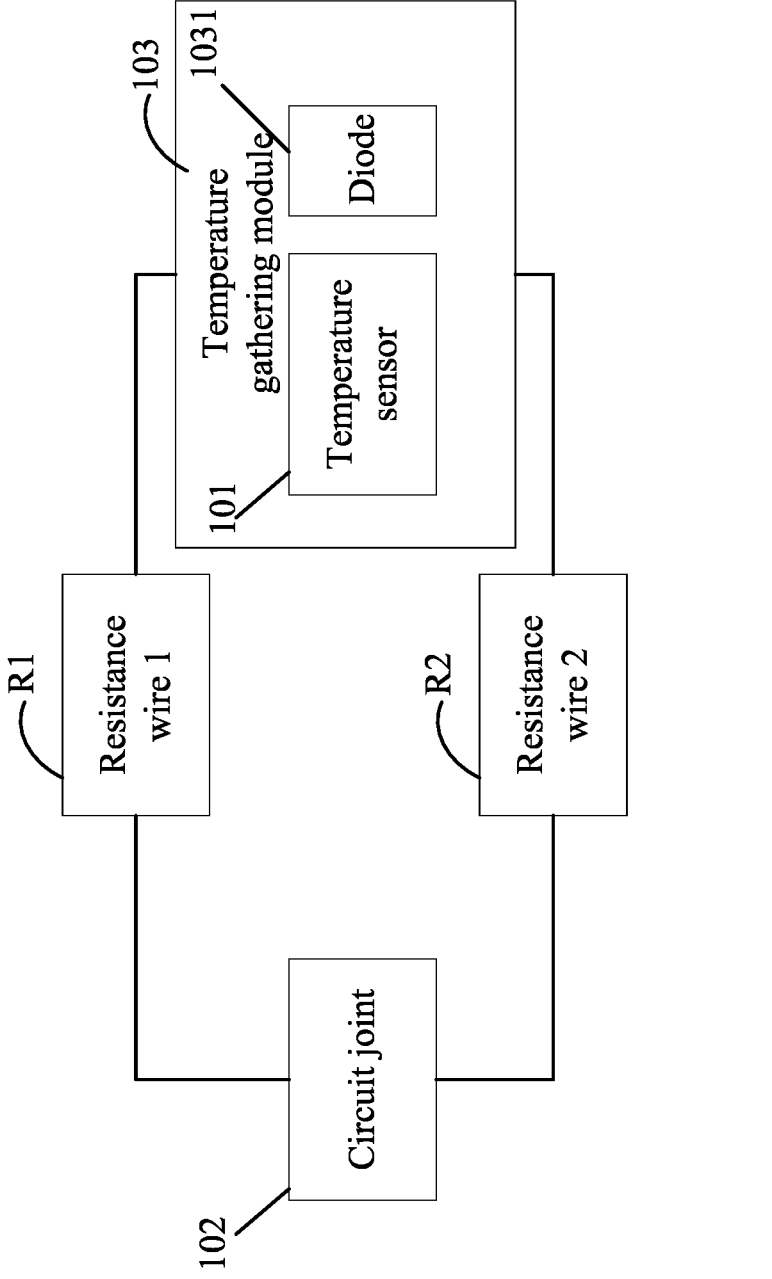
FIG. 5 illustrates a structural schematic diagram of a heated breathing-circuit.

At the step S102, the microprocessor 200 controls the heated breathing-circuit 100 to be heated in a first predetermined time period though the function-selection circuit 300, utilizing time-division multiplexing. The first predetermined time period is a time of continuously heating the heated breathing-circuit 100. The function-selection circuit 300 is configured to control tasks executed by the microprocessor 200. Further, a structure of the heated breathing-circuit 100 is shown as FIG. 5. The heated breathing-circuit 100 includes resistance wires R1 and R2, a circuit joint 102, and a temperature gathering module 103. The temperature gathering module 103 includes the temperature sensor 101, and a diode 1031. A processing-cycle time period is predetermined before the temperature control system 1000 is started to executed the temperature control method. The processing-cycle time period is composed of a first predetermined time, a second predetermined time, and a third predetermined time period. The microprocessor 200 sends the instructions thought the function-selection circuit 300 in a first predetermined time period to heat the heated breathing-circuit 100. In detail, the function-selection circuit 300 is provided with a switch. The switch is periodically to enable the microprocessor 200 to selectively electrically connected other function circuits in each period of the total processing-cycle time period.

At the step S104, the microprocessor 200 obtains a temperature signal of the heated breathing-circuit 100 in the second predetermined time period thought the function-selection circuit 300. The heated breathing-circuit 100 is provided with the temperature sensor 101. The heated breathing-circuit 100 is electrically connected with the temperature-sampling circuit 400 thought the function-selection circuit 300 in the second predetermined time period. The second predetermined time period is the time of sampling the temperature. Understandably, when the second predetermined time period arrives, the heated breathing-circuit 100 will be electrically connected with the temperature-sampling circuit 400 thought the function-selection circuit 300. The microprocessor 200 sends the instructions to the temperature-sampling circuit 400 to obtain the temperature signal thought the temperature of the temperature sensor 101 of the heated breathing-circuit 100.

At the step S106, the microprocessor 200 obtains a resistance value of the temperature sensing loop by converting the temperature signal. In detail, the microprocessor 200 performs a digital-to-analogue conversion on the temperature signal after obtaining the temperature signal. The microprocessor 200 obtains the resistance value of the temperature sensing loop according to a temperature value corresponding to the converted digital signal.

At the step S108, the microprocessor 200 controls the temperature-sampling circuit 400 to be electrically connected with the short-circuit loop 500 in the third predetermined time period thought the function-selection circuit 300, to obtain an internal resistance value of the temperature-sampling circuit 400. The total time of the first predetermined time period, the second predetermined time period, and the third predetermined time period is a processing cycle time period. The first predetermined time period is the longest of the three predetermined time period. Understandably, after the temperature value of the heated breathing-circuit 100 is obtained, the temperature-sampling circuit 400 will be electrically connected with the short-circuit loop 500 thought the function-selection circuit 300 to obtain the internal resistance of the temperature-sampling circuit 400 in the third predetermined time period for follow-up correction of the temperature value At the step S110, the microprocessor 200 obtains the resistance value of the temperature sensor 101 thought the resistance value of the temperature sensing loop, the resistance value of the resistance wire, and the internal resistance of the temperature-sampling circuit 400. The resistance value of the resistance wire is preset in the microprocessor 200. In detail, the microprocessor 200 performs a calculation on the resistance value of the temperature sensing loop, and the internal resistance of the temperature-sampling circuit 400 thought a predetermined calculation formula for calculating the resistance value of the temperature sensor 101 after obtaining the resistance value of the temperature sensing loop in the step S106, and the internal resistance of the temperature-sampling circuit 400 in the step S108. The predetermined calculation formula is $R_t = R_{all} - R_{inter} - R_1 - R_2$. In detail, $R_t$ is the resistance value of the temperature sensor 101. $R_{all}$ is the resistance value of the temperature sensing loop. $R_{inter}$ is the resistance value of the internal resistance of the temperature-sampling circuit 400. $R_1$ and $R_2$ are resistance values of the resistance wires $R_1$ and $R_2$, respectively.

At the step S112, the microprocessor 200 calculates the resistance value of the temperature sensor 101 and the temperature of the temperature sensor 101 to obtain the actual temperature value of the heated breathing-circuit 100, thought a predetermined conversion formula. Understandably, the microprocessor 200 will calculate the actual temperature value of the heated breathing-circuit 100 thought the predetermined conversion formula after obtaining the resistance value of the temperature sensor 101. The predetermined conversion formula is $$T_2 = \frac{1}{\frac{1}{T_1} - \frac{1}{B}\ln\frac{R_t}{R}}.$$

In detail, $T_2$ is the actual temperature value of a current cycle. $T_1$ is the temperature value of the temperature sensor 101. B is a thermistor constant of a negative temperature coefficient (NTC) thermistor. The NTC thermistor is the temperature sensor 101. R is the resistance value of the NTC thermistor in the temperature of $T_1$. $R_t$ is the resistance value of the temperature sensor 101.

In this embodiment, the measurement of the internal resistance value in the temperature-sampling circuit 400 are realized by adding the short-circuit loop 500, which eliminates influences of temperature-drift errors of electronic components of the temperature-sampling circuit 400 on sampling of the temperature of the heated breathing-circuit 100, and improves the accuracy of temperature control.

Figure 2:
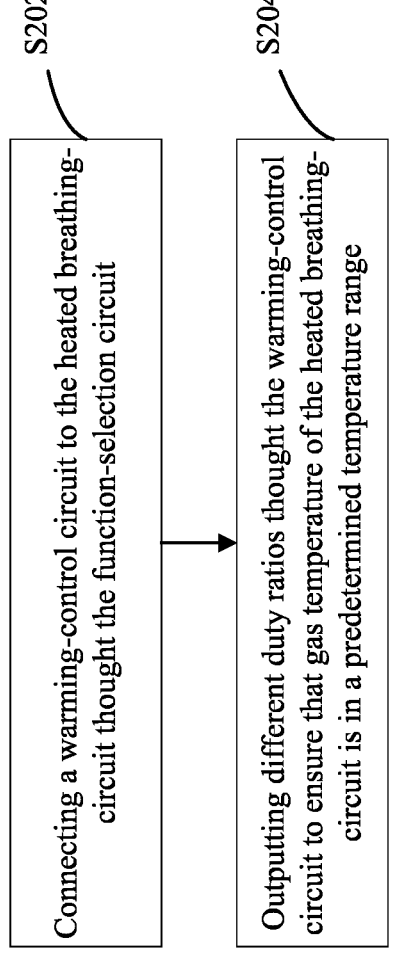
FIG. 2 illustrates a first sub-flow diagram of a temperature control method for a heated breathing-circuit.

Referring to FIG. 2, a first sub-flow diagram of a temperature control method for a heated breathing-circuit is illustrated. The method further includes follows steps S202-S204.

At the step S202, the microprocessor 200 controls a warming-control circuit to be electrically connected to the heated breathing-circuit 100 thought the function-selection circuit 300. The warming-control circuit is configured to control the delivered gas to reach different temperature ranges. Understandably, in order to effectively ensure that the temperature of the heated breathing-circuit 100 is in a predetermined temperature range, the heated breathing-circuit 100 is electrically connected with the warming-control circuit to control temperature more conveniently.

At the step S204, the microprocessor 200 controls the warming-control circuit to output different duty ratios to the heated breathing-circuit 100 that make gas temperature of the heated breathing-circuit 100 is within the predetermined temperature range. In order to control the temperature of the heated breathing-circuit 100 in the set temperature range, different duty ratios are input to control the heated breathing-circuit 100 to be heated in special cases, so as to ensure that the temperature of the heated breathing-circuit 100 is within the set temperature range.

A computer-readable storage media is also provided. The computer-readable storage media is configured to store program instructions that can be loaded and executed by a processor to perform partial or all steps of the method of temperature control for the heated breathing-circuit with the temperature correction function.

Figure 3:
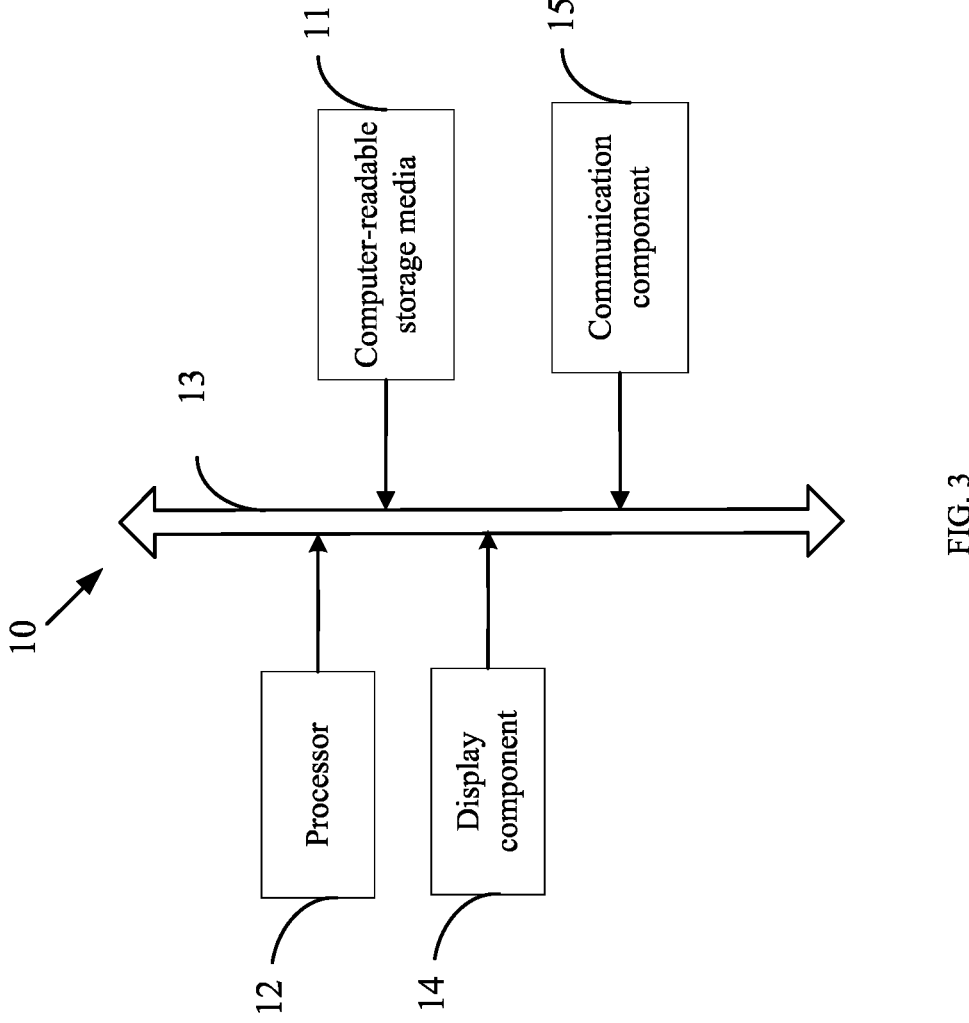
FIG. 3 illustrates an internal structural schematic diagram of a breathing assistance apparatus.

Referring to FIG. 3, an internal structural schematic diagram of a breathing assistance apparatus 10 is illustrated.

In this embodiment, the breathing assistance apparatus 10 may be a ventilator, an oxygentherapy apparatus and so on. The breathing assistance apparatus 10 includes a computer-readable storage media 11, a processor 12, and a bus 13. The computer-readable storage media 11 includes at least one type of readable storage medias, which includes a flash memory, a hard disk, a multimedia card, a card type storage (for example, an SD or a DX storage, etc.), a magnetic storage, a disks, a optical disks, etc. The computer-readable storage media 11 may in some embodiments be an internal storage unit of the breathing assistance apparatus 10, such as the hard disk of the breathing assistance apparatus 10. The breathing assistance apparatus 10 may also be an external storage device of the breathing assistance apparatus 10 in other embodiments, such as a plug-in hard disk, a smart media card (SMC), a secure digital card (SD), a flash card, etc., equipped on the breathing assistance apparatus 10. Furthermore, the breathing assistance apparatus 10 may include both the internal storage unit of the breathing assistance apparatus 10 and the external storage device. The breathing assistance apparatus 10 can not only be used to store the application software and all kinds of data installed in the breathing assistance apparatus 10, but also can be used to temporarily store the data that has been output or will be output.

The bus 13 may be a peripheral component interconnect (PCI) standard bus, or an extended industry standard architecture (EISA) bus. The bus 13 can be divided into an address bus, a data bus, a control bus and so on. For ease of presentation, only a thick line is shown in FIG. 3, but this does not mean that there is only one bus or one type of buses.

Furthermore, the breathing assistance apparatus 10 may also include a display component 14. The display component 14 can be a light emitting diode (LED) display, an LCD, a touch LCD, and an organic light-emitting diode (OLED) touch device. The display component 14 may also be appropriately referred to as a display device or a display unit, is used to display the information processed in the breathing assistance apparatus 10 as well as a user interface for displaying the visualization.

Furthermore, the breathing assistance apparatus 10 may also include a communication component 15. The communication component 15 may optionally include a wired communication component and/or a wireless communication component, such as a Wi-Fi communication component, a bluetooth communication component, etc., usually used to establish a communication connection between the breathing assistance apparatus 10 and other computer devices.

The processor 12 may be a central processing unit (CPU), a controller, a microcontroller, a microprocessor, or other data processing chip in some embodiments for running the program instruction stored in the computer-readable storage media 11 or for processing data. Specifically, the processor 12 executes the program instruction to control the breathing assistance apparatus 10 to realize the method of temperature control for the heated breathing-circuit with the temperature correction function.

Understandably, FIG. 3 only shows the breathing assistance apparatus 10 with components 11-15 and the program instruction for implementing the method of temperature control for the heated breathing-circuit with the temperature correction function. It is understood by those skilled in the field that structures shown in FIG. 3 do not constitute a limitation to the breathing assistance apparatus 10 and may include fewer or more parts than figures, or combine some parts, or different arrangement of components.

It should be noted that the embodiments number of this disclosure above is for description only and do not represent the advantages or disadvantages of embodiments. And in this disclosure, the term "including", "include" or any other variants is intended to cover a non-exclusive contain. So that the process, the devices, the items, or the methods includes a series of elements not only include those elements, but also include other elements not clearly listed, or also include the inherent elements of this process, devices, items, or methods. In the absence of further limitations, the elements limited by the sentence "including a . . . " do not preclude the existence of other similar elements in the process, devices, items, or methods that include the elements.

The above disclosed preferred embodiments of the invention are intended only to assist in the elaboration of the invention. The preferred embodiment does not elaborate on all the details and does not limit the invention to a specific embodiment. Obviously, according to the contents of this instruction manual, a lot of amendments and changes can be made. These embodiments are selected and described in detail in this specification for the purpose of better explaining the principle and practical application of the invention, so that the technical personnel in the technical field can better understand and utilize the invention. The invention is limited only by the claims and their full scope and equivalents.

The above are only the preferred embodiments of this disclosure and do not therefore limit the patent scope of this disclosure. And equivalent structure or equivalent process transformation made by the specification and the drawings of this disclosure, either directly or indirectly applied in other related technical fields, shall be similarly included in the patent protection scope of this disclosure.

The invention claimed is:

1. A breathing assistance apparatus, comprising:
a heated breathing-circuit, provided with a temperature sensor;
a temperature-sampling circuit, configured to sample a sampling temperature;
a short-circuit loop, configured to make only the temperature-sampling circuit be electrically energized;
a microprocessor; and
a function-selection circuit, configured to selectively establish different relationships among the heated breathing-circuit, the temperature-sampling circuit, the short-circuit loop, and the microprocessor; wherein the microprocessor is configured to:
controlling the heated breathing-circuit to be heated continuously in a first predetermined time period though the function-selection circuit;
obtaining a sampling temperature signal of the heated breathing-circuit in a second predetermined time period thought the function-selection circuit, wherein the heated breathing-circuit is electrically connected with the temperature-sampling circuit thought the function-selection circuit during the second predetermined time period;
obtaining a resistance value of a temperature sensing loop by converting the sampling temperature signal;
controlling the temperature-sampling circuit to be electrically connected with the short-circuit loop in a third predetermined time period thought the function-selection circuit, to obtain an internal resistance value of the temperature-sampling circuit; the first predetermined time period, the second predetermined time period, and the third predetermined time period form a processing cycle time period;
obtaining a resistance value of the temperature sensor thought the resistance value of the temperature sensing loop, a resistance value of the resistance wire, and the internal resistance of the temperature-sampling circuit; and

9 calculating the resistance value of the temperature sensor and the temperature of the temperature sensor to obtain an actual temperature value of the heated breathing-circuit, thought a predetermined conversion formula.

2. The breathing assistance apparatus of claim 1, wherein the first predetermined time period is the longest time period of the processing cycle time period.

3. The breathing assistance apparatus of claim 1, wherein the heated breathing-circuit further comprises resistance wires, a temperature gathering module, and conduit joints.

4. The breathing assistance apparatus of claim 3, wherein the temperature gathering module further comprises the temperature sensor, and a diode.

5. The breathing assistance apparatus of claim 4, wherein the temperature sensor is a thermistor.

6. The breathing assistance apparatus of claim 5, wherein the thermistor is a negative temperature coefficient (NTC) thermistor.

7. The breathing assistance apparatus of claim 6, wherein the predetermined conversion formula is $$T_2 = \frac{1}{\frac{1}{T_1} - \frac{1}{B}\ln\frac{R_t}{R}},$$

$T_2$ is an actual temperature value of a current processing cycle time period, $T_1$ is the temperature of the temperature sensor, B is a thermistor constant of the thermistor, R is the resistance value of the thermistor in the temperature of $T_1$, and Rt is the resistance of the temperature sensor.

8. The breathing assistance apparatus of claim 6, wherein obtaining the resistance value of the temperature sensor thought the resistance value of the temperature sensing loop, the resistance value of the resistance wire, and the resistance value of the internal resistance of the temperature-sampling circuit via a calculating formula, the calculating formula is $R_t=R_{all}-R_{inter}-R_1-R_2$, $R_t$ is the resistance of the temperature sensor, Rall is the resistance value of the temperature sensing loop, $R_{inter}$ is the resistance value of the internal resistance of the temperature-sampling circuit, and, $R_1$ and $R_2$ are resistance values of the resistance wire.

9. The breathing assistance apparatus of claim 1, wherein the breathing assistance apparatus further comprising a warming-control circuit, the microprocessor is further configured to:

connecting the warming-control circuit to the heated breathing-circuit thought the function-selection circuit, the warming-control circuit being configured to control output of gas with different temperature ranges.

10. The breathing assistance apparatus of claim 9, wherein the microprocessor is further configured to:

outputting different duty ratios thought the warming-control circuit to ensure that gas temperature of the heated breathing-circuit is in a predetermined temperature range.

11. A temperature control method for a heated breathing-circuit of a breathing assistance apparatus, the method comprising:

continuously controlling the heated breathing-circuit to be heated continuously in a first predetermined time period though the function-selection circuit, utilizing time-division multiplexing;

obtaining a sampling temperature signal of the heated breathing-circuit in a second predetermined time period thought the function-selection circuit, wherein the heated breathing-circuit is electrically connected with the temperature-sampling circuit thought the function-selection circuit during the second predetermined time period;

obtaining a resistance value of a temperature sensing loop by converting the sampling temperature signal;

controlling the temperature-sampling circuit to be electrically connected with the short-circuit loop in a third predetermined time period thought the function-selection circuit, to obtain an internal resistance value of the temperature-sampling circuit, the first predetermined time period, the second predetermined time period, and the third predetermined time period form a processing cycle time period;

obtaining a resistance value of the temperature sensor thought the resistance value of the temperature sensing loop, a resistance value of the resistance wire, and the internal resistance of the temperature-sampling circuit; and calculating the resistance value of the temperature sensor and the temperature of the temperature sensor, to obtain an actual temperature value of the heated breathing-circuit, thought a predetermined conversion formula.

12. The method of claim 11, wherein the predetermined conversion formula is $$T_2 = \frac{1}{\frac{1}{T_1} - \frac{1}{B}\ln\frac{R_t}{R}},$$

$T_2$ is an actual temperature value of a current processing cycle time period, $T_1$ is the temperature of the temperature sensor, B is a thermistor constant of the thermistor, R is the resistance value of the thermistor in the temperature of $T_1$, and Rt is the resistance of the temperature sensor.

13. The method of claim 12, wherein obtaining the resistance value of the temperature sensor thought the resistance value of the temperature sensing loop, the resistance value of the resistance wire, and the resistance value of the internal resistance of the temperature-sampling circuit via a calculating formula, the calculating formula is $R_t=R_{all}-R_{inter}-R_1-R_2$, $R_t$ is the resistance of the temperature sensor, Rall is the resistance value of the temperature sensing loop, $R_{inter}$ is the resistance value of the internal resistance of the temperature-sampling circuit, and, $R_1$ and $R_2$ are resistance values of the resistance wire.

14. The method of claim 11, wherein the microprocessor is further configured to:

connecting a warming-control circuit to the heated breathing-circuit, the warming-control circuit being configured to control output of gas with different temperature ranges.

15. The method of claim 14, wherein the microprocessor is further configured to:

outputting different duty ratios thought the warming-control circuit to ensure that the gas temperature of the heated breathing-circuit is in a predetermined temperature range.

16. A temperature control method for a heated breathing-circuit of a breathing assistance apparatus, comprising:

controlling the heated breathing-circuit to be heated continuously in a first predetermined time period though a function-selection circuit, the heated breathing-circuit provided with a temperature sensor;

obtaining a sampling temperature signal of the heated breathing-circuit in a second predetermined time period thought the function-selection circuit, wherein the heated breathing-circuit is electrically connected with a temperature-sampling circuit thought the function-selection circuit during the second predetermined time period;

obtaining a resistance value of a temperature sensing loop by converting the sampling temperature signal;

controlling the temperature-sampling circuit to be electrically connected with a short-circuit loop in a third predetermined time period thought the function-selection circuit, to obtain an internal resistance value of the temperature-sampling circuit; the first predetermined time period, the second predetermined time period, and the third predetermined time period form a processing cycle time period;

obtaining a resistance value of the temperature sensor thought the resistance value of the temperature sensing loop, a resistance value of the resistance wire, and the internal resistance of the temperature-sampling circuit; and calculating the resistance value of the temperature sensor and the temperature of the temperature sensor to obtain an actual temperature value of the heated breathing-circuit, thought a predetermined conversion formula.

17. The method of claim 16, wherein the first predetermined time period is the longest time period of the processing cycle time period.

18. The method of claim 17, wherein the temperature sensor is a negative temperature coefficient (NTC) thermistor.

19. The method of claim 18, wherein the predetermined conversion formula is $$T_2 = \cfrac{1}{\cfrac{1}{T_1} - \cfrac{1}{B}\ln\cfrac{R_t}{R}},$$

$T_2$ is an actual temperature value of a current processing cycle time period, $T_1$ is the temperature of the temperature sensor, B is a NTC thermistor constant of the thermistor, R is the resistance value of the NTC thermistor in the temperature of $T_1$, and $R_t$ is the resistance of the temperature sensor.

20. The method of claim 16, wherein the method further comprises:

connecting a warming-control circuit to the heated breathing-circuit thought the function-selection circuit, the warming-control circuit being configured to control output of gas with different temperature ranges; and outputting different duty ratios thought the warming-control circuit to ensure that gas temperature of the heated breathing-circuit is in a predetermined temperature range.

\* \* \* \* \*